(12) United States Patent
Tandon et al.

(10) Patent No.: US 12,559,771 B2
(45) **Date of Patent: \*Feb. 24, 2026**

(54) ACOUSTICALLY-DRIVEN BUFFER SWITCHING FOR MICROPARTICLES

(71) Applicant: The Charles Stark Draper Laboratory, Inc., Cambridge, MA (US)

(72) Inventors: Vishal Tandon, Somerville, MA (US); Charles A. Lissandrello, Newtonville, MA (US); Jenna Leigh Balestrini, Boston, MA (US); Ryan A. Dubay, Ludlow, MA (US)

(73) Assignee: The Charles Stark Draper Laboratory, Inc., Cambridge, MA (US)

( \* ) Notice: Subject to any disclaimer, the term of this patent is extended or adjusted under 35 U.S.C. 154(b) by 1582 days.

This patent is subject to a terminal disclaimer.

(21) Appl. No.: 16/359,626

(22) Filed: Mar. 20, 2019

(65) Prior Publication Data

US 2019/0292565 A1 Sep. 26, 2019

Related U.S. Application Data

(60) Provisional application No. 62/645,275, filed on Mar. 20, 2018.

(51) Int. Cl.
C12N 15/87 (2006.01)
B01L 3/00 (2006.01)
(Continued)

(52) U.S. Cl.
CPC .......... C12N 15/87 (2013.01); B01L 3/50273 (2013.01); B01L 3/502761 (2013.01);
(Continued)

(58) Field of Classification Search
CPC ................... B01L 2400/0436; B01L 3/502776
See application file for complete search history.

(56) References Cited

U.S. PATENT DOCUMENTS

| | | | | |
|---|---|---|---|---|
| 9,656,263 B2 * | 5/2017 | Laurell | ............... | G01N 33/574 |
| 11,225,638 B2 * | 1/2022 | Corso | .................... | C12M 35/02 |

(Continued)

FOREIGN PATENT DOCUMENTS

| | | | | |
|---|---|---|---|---|
| WO | WO-02072235 A1 * | 9/2002 | .......... | A61M 1/3472 |
| WO | WO-2014138739 A1 * | 9/2014 | ............ | A61M 1/362 |

(Continued)

OTHER PUBLICATIONS

Cho et al., (Biomed Microdevices, 2010, 12:855-863) (Year: 2010).*

(Continued)

*Primary Examiner* — Arthur S Leonard
(74) *Attorney, Agent, or Firm* — Wolf, Greenfield & Sacks, P.C.

(57) ABSTRACT

A system for sequential exposure of particles to different fluid streams includes an acoustic actuator device for acoustically driving one or more substrates and a microchannel device of the one or more substrates that receive particles in a first flowing fluid, moves the particles to a second flowing fluid, then moves the particles out of the second flowing fluid using acoustic radiation generated by the acoustic actuator device. The system can control residence times in the streams. According to one use, the first flowing fluid is a cell buffer and the second flowing media is an electroporation buffer. An electroporation system is placed in or downstream of the acoustic actuator device. However, in other uses, the second flowing media might be a wash buffer.

11 Claims, 11 Drawing Sheets

(51) Int. Cl.

| | |
|---|---|
| *C12M 1/42* | (2006.01) |
| *C12N 13/00* | (2006.01) |
| *C12N 15/85* | (2006.01) |
| *A61M 1/36* | (2006.01) |

(52) U.S. Cl.

CPC ....... *B01L 3/502776* (2013.01); *C12M 35/02* (2013.01); *C12N 13/00* (2013.01); *C12N 15/85* (2013.01); *A61M 1/3678* (2014.02); *A61M 2205/0244* (2013.01); *B01L 2200/0652* (2013.01); *B01L 2300/0645* (2013.01); *B01L 2300/0816* (2013.01); *B01L 2400/0436* (2013.01); *C12N 2015/8527* (2013.01); *C12N 2510/00* (2013.01)

(56) References Cited

U.S. PATENT DOCUMENTS

| | | | | |
|---|---|---|---|---|
| 11,291,756 | B2 * | 4/2022 | Fiering | A61M 1/3678 |
| 2010/0126922 | A1 | 5/2010 | Takahashi et al. | |
| 2014/0193381 | A1 | 7/2014 | Warner et al. | |
| 2017/0042770 | A1 | 2/2017 | Warner et al. | |
| 2017/0241878 | A1 | 8/2017 | Broyer et al. | |
| 2019/0119624 | A1 | 4/2019 | Tandon et al. | |

FOREIGN PATENT DOCUMENTS

| | | |
|---|---|---|
| WO | WO 2015047502 | 4/2015 |
| WO | WO 2019084000 | 5/2019 |

OTHER PUBLICATIONS

Augustsson, P., et al., "Buffer medium exchange in continuous cell and particle streams using ultrasonic standing wave focusing," Microchim. Acta, 164(3): 269-277 (2009).

Augustsson, P., et al., "Decomplexing Biofluids Using Microchip Based Acoustophoresis," Lab on a Chip, 9(6): 810-818 (2008).

Augustsson, P., et al., "Flow-Through Chip for Sequential Treatment and Analyte Elution from Beads or Cells," Twelfth International Conference on Miniaturized Systems for Chemistry and Life Sciences, 671-673 (2008).

Chang, L., et al., "Micro-/nanoscale electroporation," Lab Chip, 16(21): 4047-4062 (2016).

Chicaybam, L., et al., "An efficient low cost method for gene transfer to T lymphocytes," PLoS One, 8(3): 1-11 (2013).

Deshmukh, S., et al., "Acoustic radiation forces at liquid interfaces impact the performance of acoustophoresis," Lab Chip, 14(17): 3394-3400 (2014).

Geng, T., et al., "Microfluidic electroporation for cellular analysis and delivery," Lab Chip, 13 (19): 3803-3821 (2013).

Hümmer, C., et al., "Automation of cellular therapy product manufacturing: results of a split validation comparing CD34 selection of peripheral blood stem cell apheresis product with a semi-manual vs. an automatic procedure," J. Transl. Med., 14:76: 1-7 (2016).

International Search Report and Written Opinion, mailed on Jun. 4, 2019, from International Application No. PCT/US2019/023195, filed on Mar. 20, 2019. 17 pages.

Kaiser, A.D., et al., "Towards a commercial process for the manufacture of genetically modified T cells for therapy," Cancer Gene Ther., 22(2): 72-78 (2015).

Levine, B.L., et al., "Global Manufacturing of Car T Cell Therapy," Mol. Ther. Methods Clin. Dev., 4: 92-101 (2016).

Lissandrello, C., "Purification of Lymphocytes by Acoustic Separation in Plastic Microchannels," SLAS Technol., 23(4): 352-363 (2018).

MacLeod, D.T., et al., "Integration of a CD19 CAR into the TCR Alpha Chain Locus Streamlines Production of Allogeneic Gene-Edited Car T Cells," Mol. Ther., 25(4), 949-961 (2017).

Mueller, A., et al., "Continuous Acoustic Separation in a Thermoplastic Microchannel," J. Micromechanics Microengineering, 23: 1-10 (2013).

Ohlsson, P., et al., "Acoustic impedance matched buffers enable separation of bacteria from blood cells at high cell concentrations," Sci. Rep., 8(1): 1-11 (2018).

Pigeau, G.M., et al., "Commercial Scale Manufacturing of Allogeneic Cell Therapy," 5 (223): 1-8 (2018).

Roth, T. L., et al., "Reprogramming human T cell function and specificity with non-viral genome targeting," Nature, 559(7714): 405-409 (2018).

Rupp, L.J., et al., "CRISPR/Cas9-mediated PD-1 disruption enhances anti-tumor efficacy of human chimeric antigen receptor T cells," Sci. Rep., 7(1): 1-10 (2017).

Schumann, K., et al., "Generation of knock-in primary human T cells using Cas9 ribonucleoproteins," Proc. Natl. Acad. Sci., 112(33): 10437-10442 (2015).

Shields IV, C.W., et al., "Microfluidic cell sorting: a review of the advances in the separation of cells from debulking to rare cell isolation," Lab Chip, 15(5): 1230-1249 (2015).

Shim, G., et al., "Therapeutic gene editing: delivery and regulatory perspectives," Acta Pharmacol. Sin., 38(6), 738-753 (2017).

Tay, H.M., et al., "Microfluidic Buffer Exchange for Interference-free Micro/Nanoparticle Cell Engineering," J. Vis. Exp., 113(e54327): 1-7 (2016).

Wang, S., et al., "Micro-/nanofluidics based cell electroporation," Biomicrofluidics, 7 (011301): 1-14 (2013).

Wang, X., et al., "Clinical manufacturing of CAR T cells: foundation of a promising therapy," Mol. Ther. Oncolytics, 3 (16015): 1-7 (2016).

Yun, H., et al., "Sequential multi-molecule delivery using vortex-assisted electroporation," Lab on a Chip, 13(14): 2764-2772 (2013).

Zhao, Y., et al., "High-efficiency transfection of primary human and mouse T lymphocytes using RNA electroporation," Mol. Ther., 13(1):151-159 (2016).

Zhu, T., et al., "Electroporation based on hydrodynamic focusing of microfluidics with low dc voltage," Biomedical Microdevices, 12(1): 35-40 (2010).

International Preliminary Report on Patentability, mailed on Oct. 1, 2020, from International Application No. PCT/US2019/023195, filed on Mar. 20, 2019. 10 pages.

\* cited by examiner

0V$_{pp}$ at 300µL/min Sample Side Input and 700µL/min BTX Center Input

75V$_{pp}$ at 300µL/min Sample Side Input and 700µL/min BTX Center Input

125V$_{pp}$ at 300µL/min Sample Side Input and 700µL/min BTX Center Input

-- Channel Boundaries    --- Center Outlet Boundaries

ACOUSTICALLY-DRIVEN BUFFER SWITCHING FOR MICROPARTICLES

RELATED APPLICATIONS

This application claims the benefit under 35 USC 119(e) of U.S. Provisional Application No. 62/645,275, filed on Mar. 20, 2018, which is incorporated herein by reference in its entirety.

BACKGROUND OF THE INVENTION

Many chemical and biological processes depend on timed, sequential exposure of particles to various reagents and/or physical processes. When the particle is a colloid, or a biological particle such as a cell, liposome, or micelle, sequential exposure to a series of reagents/buffers typically requires alternating between washing/filtering and incubation steps. This procedure limits the speed at which the buffer exchange can take place. Time of exposure, however, is a critical parameter in many processes, including, for example, chemical modification of microspheres, and transfection/transduction of cells.

One cell transfection process, for example, is electroporation. This process is often used to temporarily permeabilize cells in order to facilitate the entry of cargo, which can be used to alter or genetically modify the cells. One of the major challenges with electroporation, limiting its use for clinically-relevant cell bioprocessing, is that the process often results in significant amounts of dead cells due to heating and formation of electrochemical reaction products, reducing the ultimate yield of usable cells. To mitigate these issues, cells are often electroporated in specialized, (typically) low-conductivity electroporation buffers. The use of such buffers reduces the amount of electrical current that must be generated to maintain the magnitude of the electric fields required for permeabilization, and therefore reduces both the heat and electrochemical reaction products generated at the electrodes. However, most cell types can only survive for a very limited amount of time in these buffers (~hours), so limiting the residence time of cells in low-conductivity electroporation buffers is crucial.

In addition, some electroporation applications require the timed, sequential delivery of multiple payloads. Traditional bulk electroporation relies on centrifugation followed by resuspension of cells in new media to effect buffer, reagent, and payload exchanges. In addition to the touch labor involved, these exchanges require the cells to reside in each buffer for at least several minutes, which in some cases (as discussed above) can be detrimental to cell health, and also limits control of payload entry kinetics and access to very short (seconds or less) exposure times.

Most electroporation protocols that involve using a specialized low conductivity buffer (See Zhu, T. et al., *Electroporation based on hydrodynamic focusing of microfluidics with low dc voltage*, Biomedical Microdevices, 12(1), pp. 35-40, 2010) do not provide a method for rapid buffer exchange. Typically, cells are centrifuged and resuspended. This is the case both for bulk systems, and commercial flow electroporation systems. One group has used vortex-assisted electroporation for sequential delivery of small molecules (see Yun, H. & Hur, S. C., Sequential multi-molecule delivery using vortex-assisted electroporation. Lab on a Chip, 13(14), p. 2764, 2013, available at: hypertext transfer protocol://xlink.rsc.org/?DOI=c3lc50196e).

U.S. patent application Ser. No. 16/168,464, filed Oct. 23, 2018, by Tandon, et al., concerns acoustophoretic manipulation in a "contactless" method for manipulating cell position. Its general purpose is to enhance the process of cargo delivery to cells, via electroporation. The cargo can include, but is not limited to, DNA, RNA, proteins, transposons, and biomolecule complexes, to list some examples. This device uses the acoustic radiation force generated by an ultrasonic transducer to position cells along the central streamline of flow between a pair of electroporation electrodes. This acoustically-mediated migration enables precise control of cell or vesicle positioning in the electric field.

SUMMARY OF THE INVENTION

This invention uses parallel, co-flow streams in a microfluidic device combined with acoustic manipulation of particles to enable rapid buffer switching, enabling precise control over the residence time of particles in each buffer stream. It is possible to even have very short residence times (of seconds or less). One key advantage of acoustic focusing is that it allows manipulation of cell motion with respect to the streams, enabling concentration of cells and migration of cells out of one buffer and into another.

This invention can also make possible sequential exposure of the particles to several different buffer/reagent streams, with controlled residence times. Parallel streams (2 or more) are established in a microfluidic device in a laminar flow regime, for example. Mixing between the streams is thus primarily due to diffusion and dispersion, and is minimal over the time scales considered. An acoustic radiation field generated by a piezoelectric transducer or surface acoustic wave transducer, for example, can be used to manipulate particles with respect to the streams, and to move the particles from one stream to another.

In general, the invention concerns the use of acoustic radiation to temporarily move particles, such as cells or other structures, out of an input fluid stream and into another, e.g, electroporation or wash fluid stream, perform some operation on the particles, such as electroporation or washing, and then move the particles out of the fluid stream, preferably in one continuous process.

One illustration relates to electroporation and employs 3 parallel flow streams established in a microfluidic device. The center stream might comprise a specialized electroporation buffer, and the sheath streams might comprise target cells suspended in their favored or preferred or first medium. Acoustic radiation pressure supplied by a piezoelectric transducer is used to drive the cells (also referred to herein as structures or particles) from the sheath stream into the center stream, where they are electroporated via electrodes patterned on the channel walls, for example. Cells exit through the center of a trifurcating outlet, and are introduced into the side streams of a second sheath flow channel. In that channel, the center stream comprises the cells' favored (preferred) medium or a second medium. A second payload could be present in the second medium. Acoustic radiation is then used to drive the cells into the center stream, returning them to their preferred media. This process can be repeated multiple times to achieve multiple buffer exchanges.

In general, according to one aspect, the invention features a system for sequential exposure of particles to different fluid streams. The system comprises an acoustic actuator device for acoustically driving one or more substrates and a microchannel device of the one or more substrates that receives particles in a first flowing fluid, moves the particles to a second flowing fluid, then moves the particles out of the second flowing fluid using acoustic radiation generated by the acoustic actuator device.

Preferably, the system controls residence times in the streams. And, also, the first flowing fluid and the second flowing fluid are preferably merged in a laminar flow regime.

Different operations can be performed. For example, the first flowing fluid can be a cell buffer and the second flowing fluid can be an electroporation buffer. On the other hand, the first flowing fluid could be a cell buffer and the second flowing fluid could be a wash buffer.

An electroporation system is preferably located in or downstream of the acoustic actuator device.

In the current embodiments, the microchannel device establishes a sheath flow of the first flowing fluid on either side of the second flowing fluid.

In one implementation, the particles are moved out of the second flowing fluid and back into the first flowing fluid.

In one implementation, the particles are moved out of the second flowing fluid and into a third flowing fluid.

In general, according to another aspect, the invention features a method for sequential exposure of particles to different fluid streams. This method comprises flowing a first fluid and a second fluid through a microchannel device of one or more substrates, acoustically moving particles in the first fluid to a second fluid, and moving the particles out of the second flowing fluid, such as back into the first fluid or into a third fluid.

In general, according to another aspect, the invention features a system for sequential exposure of particles to different fluid streams, comprising one or more microchannel devices formed in one or more substrates and two acoustic transducers that move particles between different fluids flowing through the one or more microchannel devices.

In general, according to another aspect, the invention features a system for sequential exposure of particles to different fluid streams, comprising a microchannel device formed in a substrate and an acoustic transducer that moves particles between different fluids flowing through the microchannel device. A switching channel of the microchannel device has a changing geometry along its length to create acoustic focusing and defocusing regions.

In general, according to still another aspect, the invention features a system for sequential exposure of particles to different fluid streams, comprising two or more parallel microchannel devices formed in a substrate and an acoustic transducer that moves particles between different fluids flowing through the microchannel devices.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The draw-ings are not necessarily to scale; emphasis has instead been placed upon illustrating the principles of the invention. Of the drawings.

Figure 1:
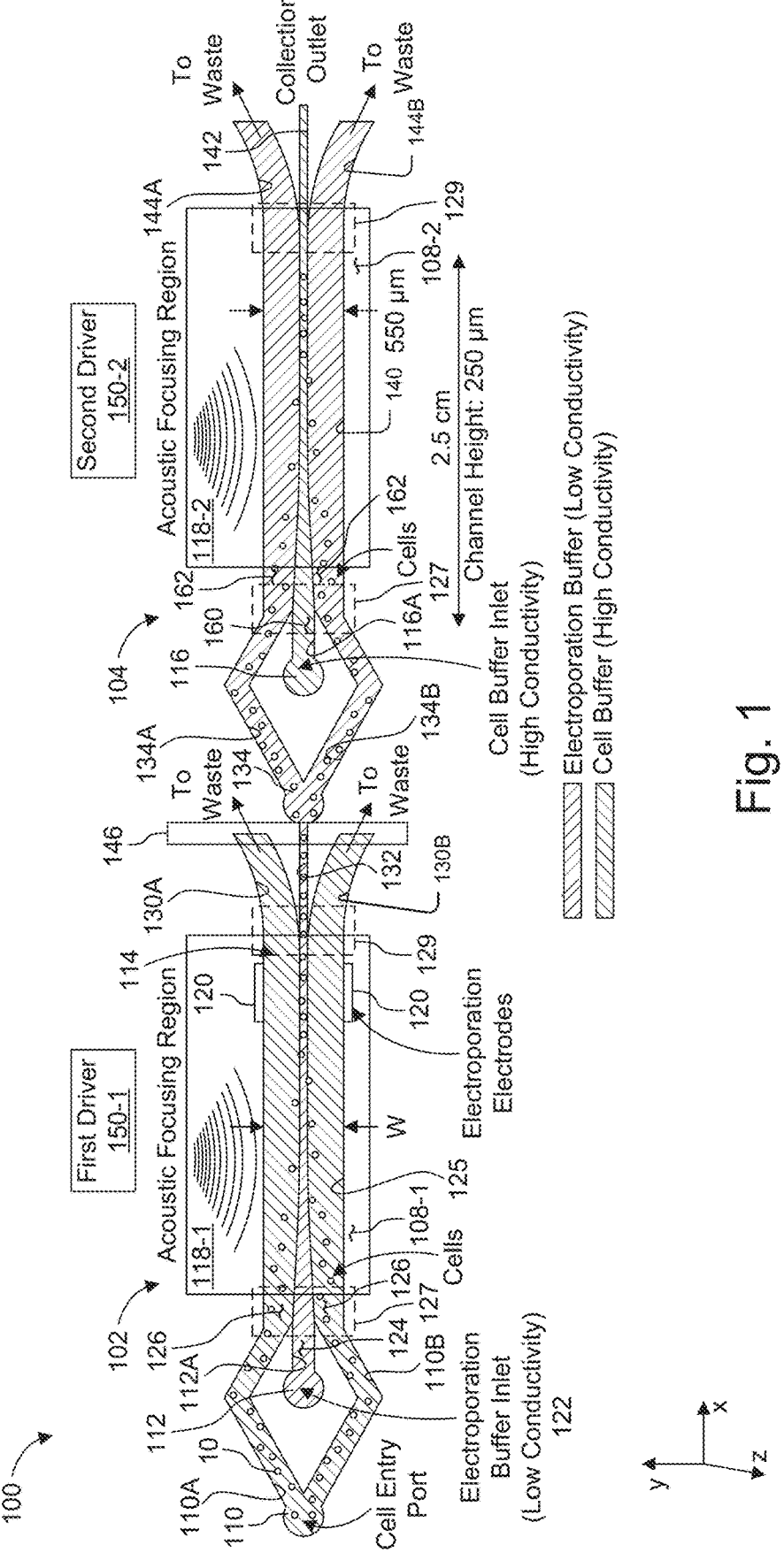
FIG. 1 is a schematic view showing a two-stage, acoustically-driven, rapid buffer exchange system used for electroporation of particles, such as cells.

DETAILED DESCRIPTION OF THE
PREFERRED EMBODIMENTS

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

It will be understood that although terms such as "first" and "second" are used herein to describe various elements, these elements should not be limited by these terms. These terms are only used to distinguish one element from another element. Thus, an element discussed below could be termed a second element, and similarly, a second element may be termed a first element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In many of its aspects, the invention relates to approaches for transferring one or more material(s), referred to herein as "cargo" or "payload", into cells. Examples of cargo materials include but are not limited to small molecules, chromosomes, DNA, RNA, (e.g., mRNA, siRNA, gRNA, ssRNA), other genetic materials, oligomers, biomarkers, proteins, transposons, biomolecule complexes, small molecules, therapeutic agents, and so forth.

In specific embodiments, the invention relates to the introduction of small molecules (DNA, RNA, etc.) into particles, i.e., cells, e.g., eukaryotic cells, by a technique referred to as "transfection". Typically, a non-viral method, transfection often involves electroporation, an approach that permeabilizes cells. Opening transient pores or "holes" in the cell membrane allows the uptake of the cargo material and thus can alter or genetically modify the cells.

Aspects of the invention can be applied or adapted to transferring cargo to particles other than cells, such as, for example exosomes, liposomes, micelles, and organelles.

FIG. 1 shows a two-stage, acoustically-driven, rapid buffer exchange system 100 used for electroporation of cells, which has been constructed according to the principles of the present invention.

This example comprises two or more connected microchannels 102, 104. Typically, the channels are fabricated from a hard polymer substrate or substrates 108, such as polystyrene (see also FIG. 2), or other hard substrates such as silicon, glass, and quartz. The prototypical two-channel system is described here, but additional channels can be added in kind.

In the illustrated example, each of the microchannels 102, 104 is fabricated in a separate substrate 108-1, 108-2.

Each microchannel 102, 104 supports a sheath or co-flow, with a center stream 124 and streams 126 on either side. In specific examples, the center stream 124 has a composition that is different from the composition of the side streams 126. Flow is maintained in the laminar regime, so mixing between the streams is minimal.

In order to maintain this laminar flow, the fluid velocities of the center stream 124 and the sheath or side streams 126 are such that the Reynolds number, Re, in the system is small (Re<<~2000) in the region of the trifurcated inlets in convergence region 127. Preferably, Re is less than 500 and is preferably less than 10.

The microchannels 102, 104 may be rectangular in cross section with width and height dimensions that range from 100 micrometers ($\mu$m) to 1000 $\mu$m. The length of each of the microchannels 102, 104 ranges from 5 millimeters (mm) to 30 mm.

Other embodiments are possible, however. Another example has a concentric flow geometry wherein the sheath stream 126 surrounds the center stream 124 on all sides. Particles, such as cells 10, initially introduced into the one or more sheath streams 126, e.g., at an input region such as inlet port 110, can range in diameter from 100 nanometers (nm) to 25 $\mu$m. For example, T-cells, a typical particle for electroporation transfection, range in size from about 6 $\mu$m to 12 $\mu$m.

In one application, the system 100 is used to rapidly move cells into and out of a specialized electroporation buffer, each microchannel has two inlets 110, 112 and a trifurcating outlet 114. Electroporation buffer is introduced directly into the first microchannel 102 through inlet 112 and forms or comprises the center stream. Cells in their preferred media, i.e., cell buffer, are introduced through the cell inlet 110. The media input into the inlet is bifurcated into two cell subchannels 110A, 110B. The cell sub channels 110A, 110B diverge from each other in the y-axis direction and then converge as they progress in the positive x-axis direction.

The cell buffer and the electroporation buffer generally differ from each other in terms of how long the cells can survive in the respective buffers. An example of a cell buffer for T cells would be TexMACS (sold by Miltenyi Biotec Inc.) or RPMI (sold by Thermo Fisher Scientific Inc.). Such cell buffer typically contains physiological salt concentrations that match cell osmolarity and nutrients. On the other hand, an example of an electroporation buffer would be BTX low-conductivity buffer (sold by BTX). Such electroporation buffer typically has lower salt concentration to reduce the conductivity, but has added sugars to reduce osmotic shock to the cells.

The cell sub channels 110A, 110B converge toward each other, on either side of an electroporation buffer subchannel 112A to create a trifurcated inlet in the convergence region 127. In this way, all three subchannels 110A, 110B, 112A deliver their flow into a switching channel 125. The flow of streams 126, containing the cells, converges around the center stream 124 as two side sheath streams of the flow.

At the other distal end of the first microchannel 102, the switching channel 125 delivers flow to two side outlet subchannels 130A, 130B in divergence region 129. Here, the subchannels 130A, 130B diverge from each other in the y-axis direction as they progress in the x-axis direction and also diverge from a center outlet subchannel 132. The two side outlet subchannels 130A, 130B carry flow largely from the original sheath input streams 126 and exit as waste or are collected for reuse.

The center outlet subchannel 132 carries flow from the center stream of the switching channel. It contains the cells 10 in the electroporation buffer.

Here, also laminar flow is preferably maintained. The fluid velocities within a divergence region 129 are such that the Reynolds number, Re, in the system is small (Re<<~2000) in the region of the trifurcated outlets in divergence region 129. Preferably, Re is less than 500 and is preferably less than 10.

The center outlet subchannel 132 of the first microchannel 102 directs flow to inlet 134 of the second microchannel 104, preferably fabricated in a separate substrate 108-2. The second microchannel inlet 134 bifurcates into two cell subchannels 134A, 134B. The cell sub channels 134A, 134B diverge from each other in the y-axis direction and then reconverge as they progress in the positive x-axis direction.

The cells' preferred media or a secondary media (possibly containing a different biomarker or cargo to be transfected) is introduced into the other inlet 116 of the second microchannel 104. The electroporated cell sub channels 134A, 134B converge toward each other, on either side of a cell buffer subchannel 116A, which carries the flowing media in the positive x-axis direction.

The electroporated cell sub channels 134A, 134B and the cell buffer subchannel 116A deliver their flow into a second switching channel 140. Here, the cells 10 are directed, from the side streams 162, to the center stream 160 of the second switching channel 140 of the second microchannel 104. As before, the Reynolds number, Re, is small (Re<<~2000) in the region of the trifurcated inlets in convergence region 127. Preferably, Re is less than 500 and is preferably less than 10.

Cells can be collected from the center outlet subchannel 142 of the second microchannel 104. Two lateral outlet subchannels 144A, 144B, at the end of the switching channel 140 and on either side of the center outlet subchannel 142, carry fluid to waste or a collection arrangement for reuse.

Alternatively, cells can be directed toward an additional microchannel and so forth, depending on the number of buffer exchanges that are desired. Typical input flow rates range from 1 microliter per minute ($\mu$l/min) to 1 milliliter per minute (ml/min).

The system is provided with an acoustic actuator device. Specifically, each of the microchannels 102, 104 are driven by separate piezoelectric transducers or surface acoustic wave transducers 118-1, 118-2, in one embodiment.

In one example, the substrates 108-1, 108-2 are bonded to separate lead zirconate titanate piezoelectric transducers 118-1, 118-2 using cyanoacrylate adhesive, and it is shorter than the microchannel. The transducers 118-1, 118-2 are connected to and driven by separate drivers 150-1, 150-2, each of which includes a radio frequency amplifier which is driven by a function generator that creates the sinusoidal signal which excites the respective channel 102, 104. This device configuration has been shown to support an acoustic resonance frequency between 900 to 990 kHz, where a stable standing pressure wave is generated across the width of each of the switching channels 125, 140. The transducers and microchannel substrates are also preferably mounted to aluminum plates which acts as a heat sink. A thermoelectric cooler (TEC) element and base plate sit beneath the aluminum plate. A thermistor is connected on top of the transducer near the microchannel, which is connected to a TEC controller along with the TEC, to make a closed-loop temperature control system. The temperature is preferably held at approximately 26° C.

An acoustic isolator 146 prevents acoustic energy from each of the acoustic transducers 118-1, 118-2 from affecting the other microchannel. This prevents cross-talk between the two microchannels and allows them to be separately driven and tuned. In the present example, isolation is achieved by fabricating the microchannels 102, 104 in separate substrates 108-1, 108-2 and then connecting the substrates with flexible tubing to avoid acoustic crosstalk.

These transducers 118-1, 118-2 are actuated by separate drivers 150-1, 150-2. Each of these drivers applies a separately tunable sinusoidally varying voltage, for example. The frequency is chosen such that a stable standing pressure wave is generated across the width of each switching channel 125, 140 of the respective microchannel 102, 104 (transverse to the fluid flow direction).

For the fundamental focusing mode there is a single pressure node in the fluid. The acoustic radiation pressure exerts a force on the cells in the direction of the pressure node. This results in the migration of cells out of the side streams and into the center stream, toward the centerline of the cross-section of the channel. In the first microchannel 102, this action results in cells moving out of their preferred buffer and into the electroporation buffer, where they are electroporated. In the second microchannel 104, this action results in cells moving out of the electroporation buffer and back into their preferred or a new buffer. This results in a residence time of cells in the electroporation buffer of seconds or less.

A pair of electroporation electrodes 120 (see also FIG. 3) can be positioned in the region between the trifurcated inlet and trifurcating outlet of the first microchannel 102; for example, halfway between the trifurcation inlet and trifurcation outlet. If multiple stages of electroporation, with multiple sequential payloads being required, electrodes may also be fabricated in the 2nd and any additional microchannels, so long as the final microchannel returns cells to their preferred buffer. The electrodes 120 are placed such that cells pass through the electroporation field after being focused into the electroporation buffer in the center stream 124 of in the switching channel 125.

The electrodes 120 may be patterned using photolithographic processes onto the floor and ceiling of the switching channel 125, or onto the sidewalls of the channel 125. Electrode area (especially the dimension along the flow axis (x-axis direction in FIG. 1) of the channel) and flow rate determine the residence time of cells in the electric field. Chosen residence times can vary from 100 microseconds ($\mu$s) to about a second. Alternatively, "remote electrodes" can be used, comprising fluidic connections from open ports to the main channel, and wire electrodes placed in the ports (such a configuration requires Faradaic current to pass through the electrodes). An AC (for example, sinusoids or pulse trains with periods/pulse widths ranging from 10 ns to 100 s of microseconds) or a DC electric field is established and remains active while cells flow through the device. The magnitude of the field is tuned for the specific cell type to a value sufficient to achieve permeabilization, and is typically in the range of 2-200 kV/m.

Cargo can be mixed into either the electroporation buffer introduced into the first microchannel 102 at inlet 112, or with the cells in the preferred cell buffer that is introduced into the cell inlet 110. The former enables tuning of the cells' exposure times to the cargo by adjusting the timing of transit into the second microchannel.

In some embodiments, the individual microchannels are fabricated separately, connected fluidically by polymer tubing, and are acoustically-actuated independently. The individual microchannels might even be fabricated on the same substrate and actuated together using a single piezoelectric transducer. In some embodiments the "waste" streams in the two side outlet subchannels 130A, 130B from the first microchannel 102, containing the cells' preferred media, are directed and coupled into the center stream via inlet 116 of the second microchannel 104 (instead of a second pump delivering media directly into the center stream of the second microchannel). In some embodiments, multiple sequential microchannel setups are laid out in parallel with manifolds for introducing cells and buffer, increasing throughput.

Figures 2A, 2B:
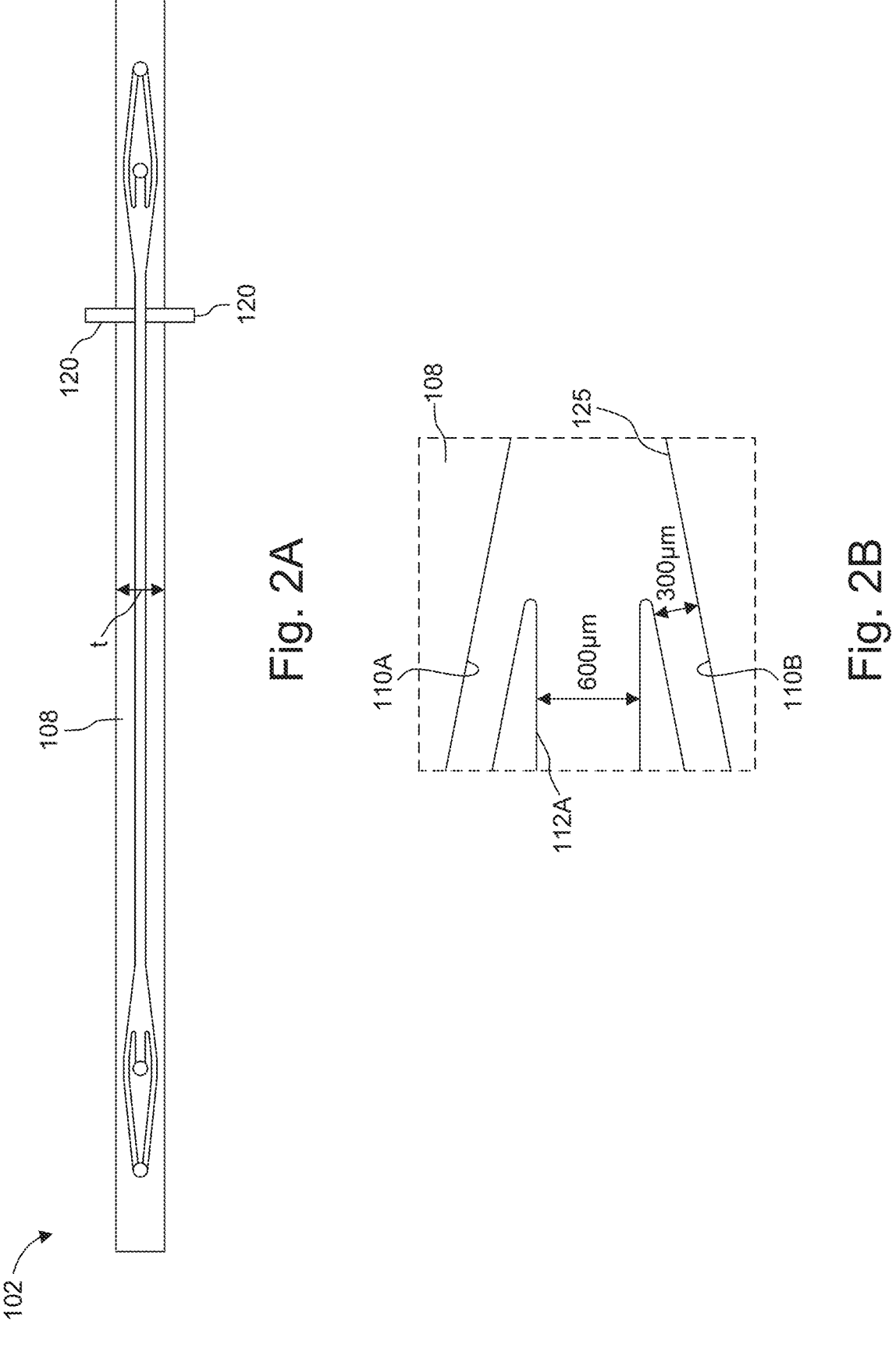
FIG. 2A is scale plan view of an example microchannel including the electroporation electrodes, in which dimensions are shown in millimeters.
FIG. 2B shows the region of the microchannel where the cell sub channels converge toward each other, on either side of a electroporation buffer subchannel to create a trifurcated inlet.

FIG. 2A is scale plan view of an example microchannels 102 including the electroporation electrodes 120. Dimensions are shown for an exemplary embodiment in millimeters.

FIG. 2B shows the region where the cell subchannels 110A, 110B converge toward each other, on either side of an electroporation buffer subchannel 112A to create a trifurcated inlet.

Figure 3:
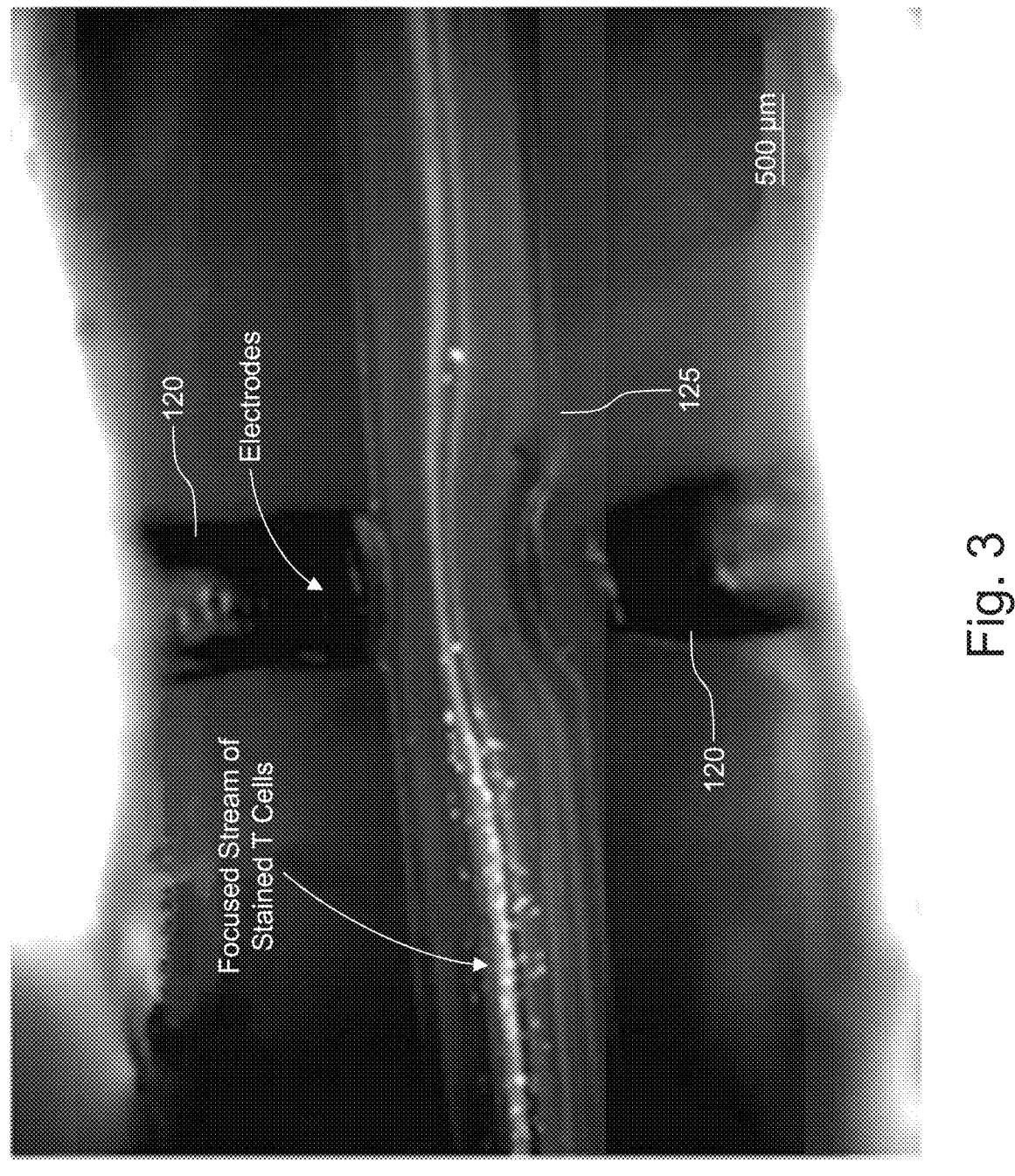
FIG. 3 is a microscope image showing fluorescently-stained T cells acoustically focused between two electroporation electrodes in one embodiment of this invention.

FIG. 3 is an image from the region of the electrodes showing focused stained. T cells flowing between the electroporation electrodes 120.

Figure 4A:
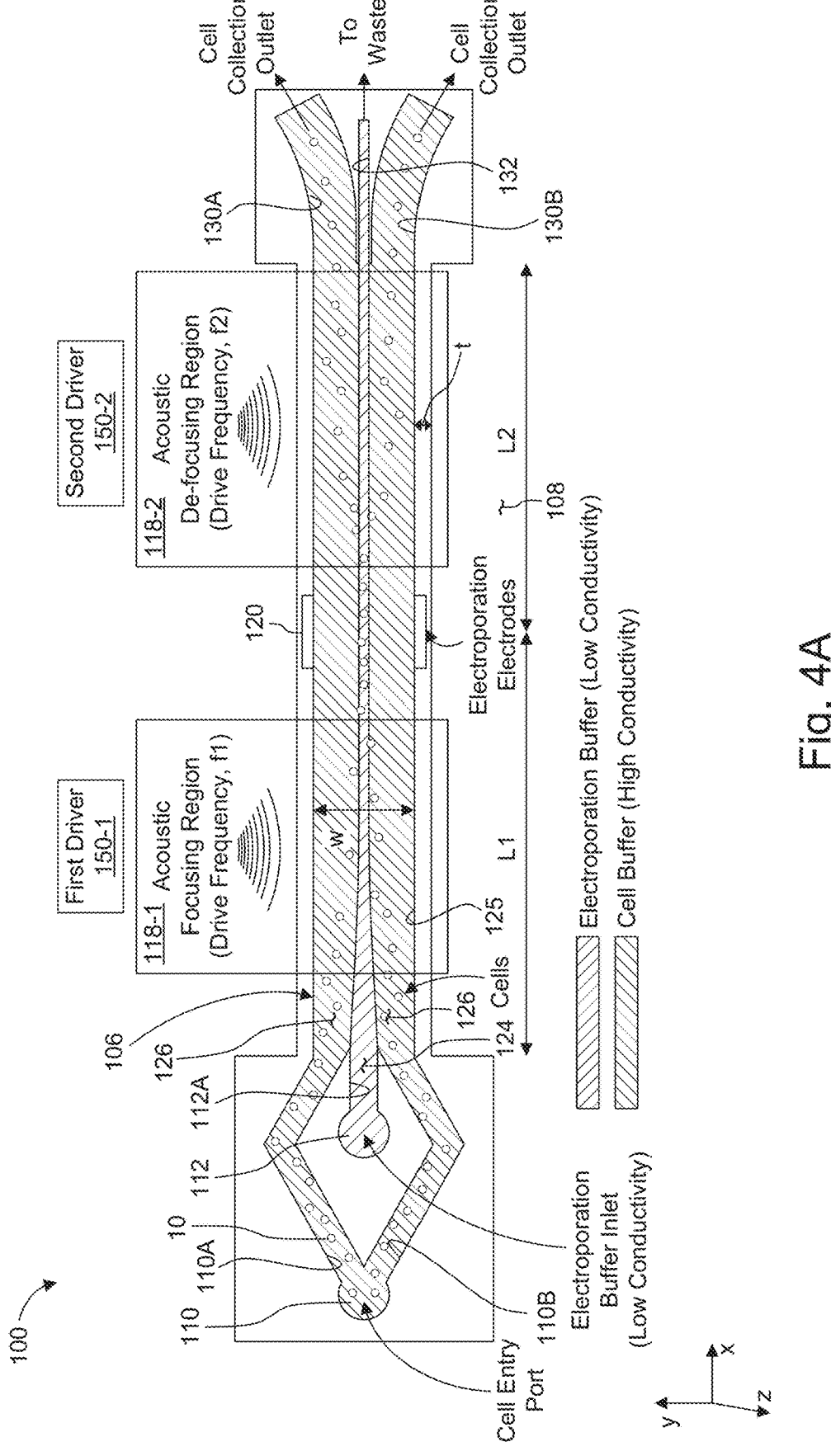
FIGS. 4A and 4B are schematic views of two further embodiments of the acoustically-driven, rapid buffer exchange system used for electroporation of cells.
Figure 4B:
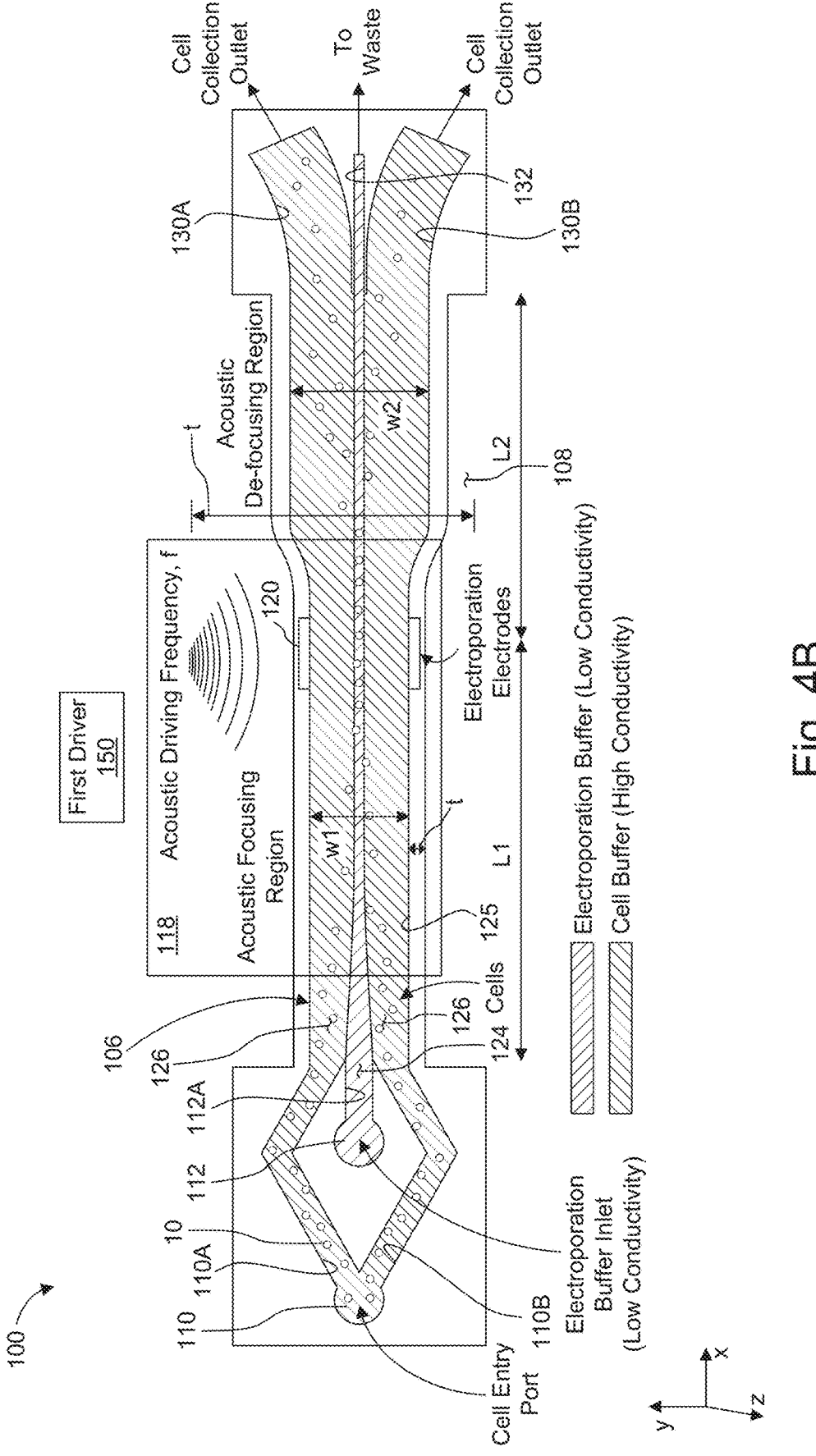

FIGS. 4A and 4B show two alternate embodiments of the rapid buffer exchange system 100. Here, in a compound microchannel 106, the cells are focused into the center stream for electroporation, and then focused back into the outer stream (called "de-focused" here) for collection.

In more detail, electroporation buffer is introduced directly into the compound microchannel 106 through inlet 112 and comprises the center stream of the sheath flow, as shown in FIG. 4A. Cells in their preferred media are introduced through the cell inlet 110. The media input into the inlet is bifurcated into two cell subchannels 110A, 110B. The cell sub channels 110A, 110B diverge from each other in the y-axis direction and then converge as they progress in the positive x-axis direction.

The cell sub channels 110A, 110B converge toward each other, on either side of an electroporation buffer subchannel 112A to create a trifurcated inlet. In this way, the subchannels 110A, 110B, 112A deliver their flow into a compound switching channel 125. The flow 126, containing the cells, converges around the center stream 124 as two side sheath streams of the flow as in previous embodiments.

At the other distal end of the first microchannel 102, the switching channel 125 delivers flow to two side outlet subchannels 130A, 130B, which diverge from each other in the y-axis direction as they progress in the x-axis direction. The two side outlet subchannels 130A, 130B carry flow largely from the original sheath streams 126, but in this example, the cells have been moved into the sheath streams 126 upstream of the side outlet subchannels 130A, 130B.

The long compound switching channel 125 is divided into two regions by a set of electroporation electrodes 120 on either lateral side of the channel at a distance L1, measured along the x-axis, from the trifurcating inlet, which distance, for example, can range from 20 to 40 mm. The channel has a width of w, which can range from 420 to 740 μm. Acoustic actuation at frequency, f1, which typically ranges from 400 to 1000 kHz, is applied by the first driver 150-1 to the first acoustic wave transducers 118-1 and is used to drive cells to the center, low-conductivity stream upstream of the electroporation electrodes 120. In the region downstream of the electrodes 120, a different frequency, f2, typically greater than f1, by a a factor of 1.5 to 2.5, for example, is applied by the second driver 150-2 to the second acoustic wave transducers 118-2, which is used to drive the cells out of the center stream.

The center outlet subchannel 132 at the distal end of the microchannel 102 carries flow from the center stream of the switching channel, e.g., to waste or recycling.

In FIG. 4B, a single acoustic driving frequency is used, but the channel downstream of the electrodes 120 is wider, having a width w2 that is greater than w1 (the width upstream of electrodes 120) by a factor of 1.5 to 2.5. This alters the nodal structure of the soundwaves in the channel and achieves the similar forcing of the cells to the side streams.

In both the FIGS. 4A and 4B embodiments, the width t of the substrate 108 with respect to the width of the fluid channel w, w1, w2 is an important parameter. It ranges from 550 to 1050 μm.

In still a further embodiment, the microchannel(s) continue to sit atop a piezoelectric transducer (or surface acoustic wave transducer) for generating the acoustic standing mode which acts on the microparticles (or cells) in the microchannel(s). However, this embodiment does not employ a set of electroporation electrodes for generating electric fields in the fluid. Such a configuration, i.e., without electroporation electrodes, is useful for "washing" cells or for transferring them from one media to another, for example. It can represent a good alternative to the conventional method that involves spinning down the microparticles (cells) in a centrifuge, removing the supernatant, adding the second buffer, and resuspending the microparticles.

Figure 5:
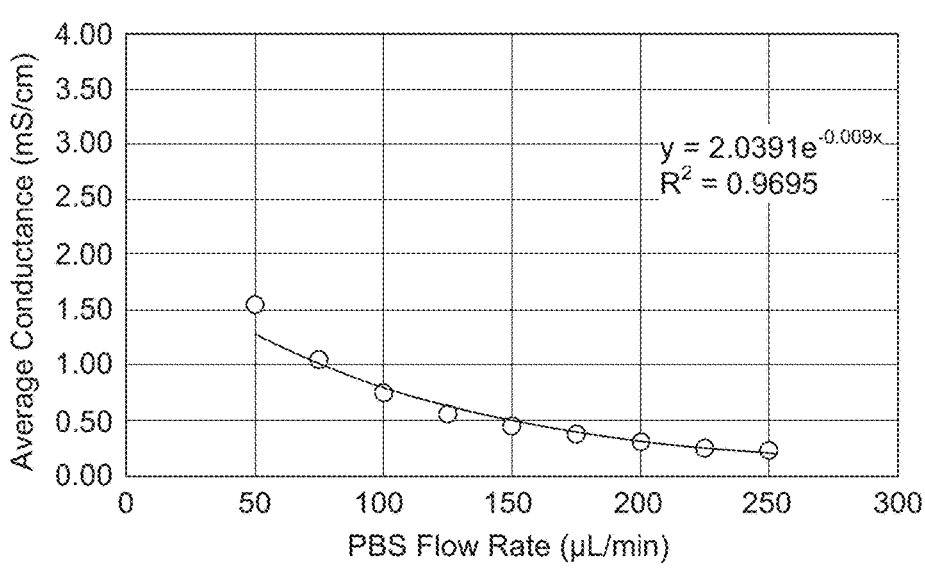
FIG. 5 is a plot of average conductance (mS/cm) as a function of flow rate for 10 mL syringe, which was varied from 50 to 250 µL/min in which the center outlet flow fraction was held constant ~41%.

In an embodiment of the invention configured to transfer cells from high-conductivity cell culture buffer to low-conductivity electroporation buffer, FIG. 5 shows how much the center stream is contaminated with ions from the side streams due to diffusion as a function of flow rate. At higher flow rates, there is less time for diffusion, and less contamination. Average conductance (mS/cm) of the collected center stream at the output, which comprises predominately cells in electroporation media, is plotted as a function of flow rate of the side streams, which was varied from 50 to 250 μL/min while the center outlet flow fraction was held constant ~41%. The results demonstrate that increasing the flow rate of phosphate-buffered saline (PBS), and therefore the total flow rate and average flow velocity through the system, decreased the degree of contamination of the BTX electroporation buffer output, as measured by conductance.

Figures 6A, 6B, 6C:
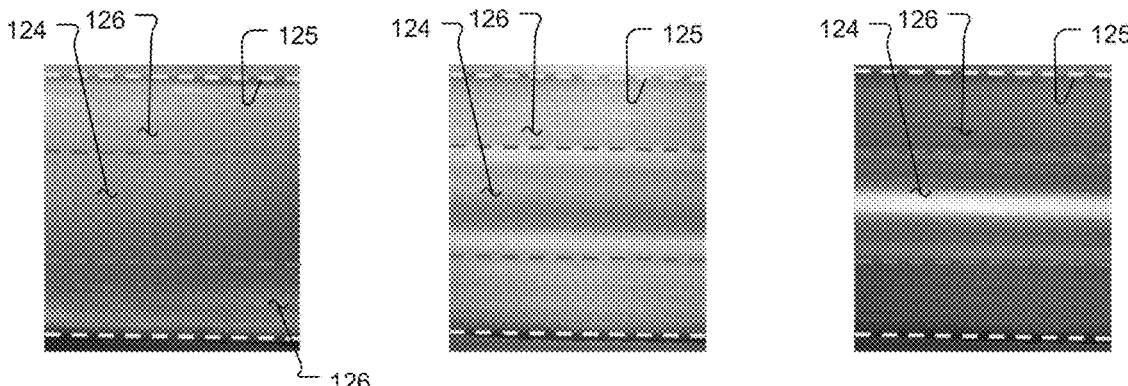
FIGS. 6A, 6B, and 6C are top down images of a switching channel.

FIGS. 6A, 6B, and 6C are top down images of a switching channel 125 showing that increasing the voltage applied to the transducer improves the focusing of cells that were originally introduced in the side inlet. At 0 V, there is no focusing of cells into the center of the channel, at 75 V there is moderately good focusing, and at 125 V there is a bright band at the center of the channel showing focused cells.

Figures 6D, 7:
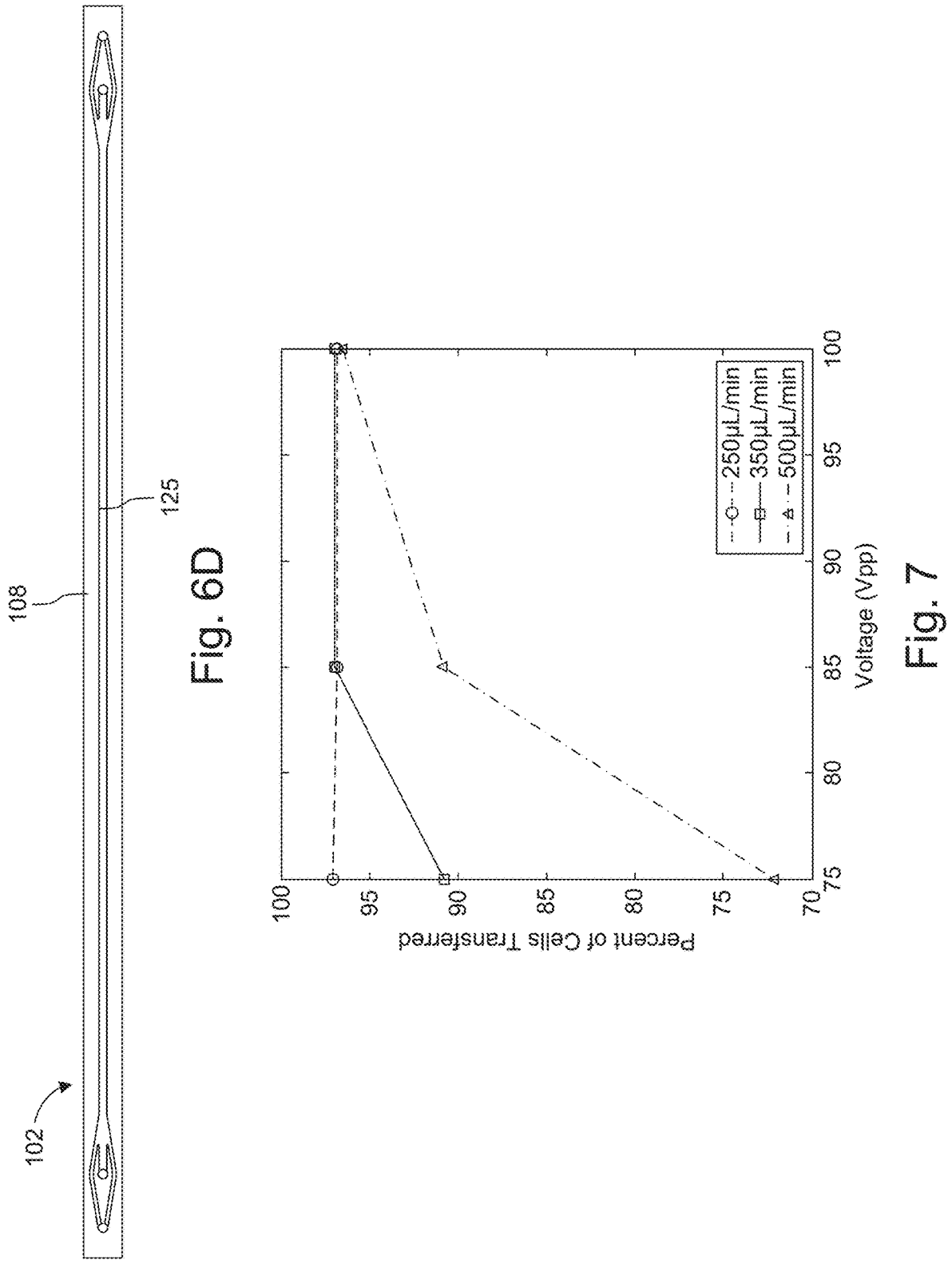
FIG. 6D is scale plan view of an example microchannel from which the images were generated (dimensions are shown in millimeters).
FIG. 7 is a plot of cells transferred in percent as a function of voltage in which $$\% \text{ Transferred} = \frac{\text{Cells in Center}}{\text{Cells in Center} + \text{Cells in Side}}.$$

FIG. 6D shows the microchannel 102, and its dimensions, that were used in the collection of the images of FIGS. 6A-6C.

FIG. 7 is a plot of percent of cells transferred as a function of voltage. In the experiment, cells initially introduced in the side inlet are moved and collected in the center outlet as a result of the acoustic excitation. Input flow rate was increased from 250 μl/min to 500 μl/min, and 3 voltages were applied to the transducer. Cells in the collected outputs were counted to assess the quality of focusing by comparing cell counts in the center output to the total cell count. At the highest tested flow rate of 500 μl/min, quality of the buffer exchange of cells is maintained by increasing the applied voltage to the transducer.

Figure 8:
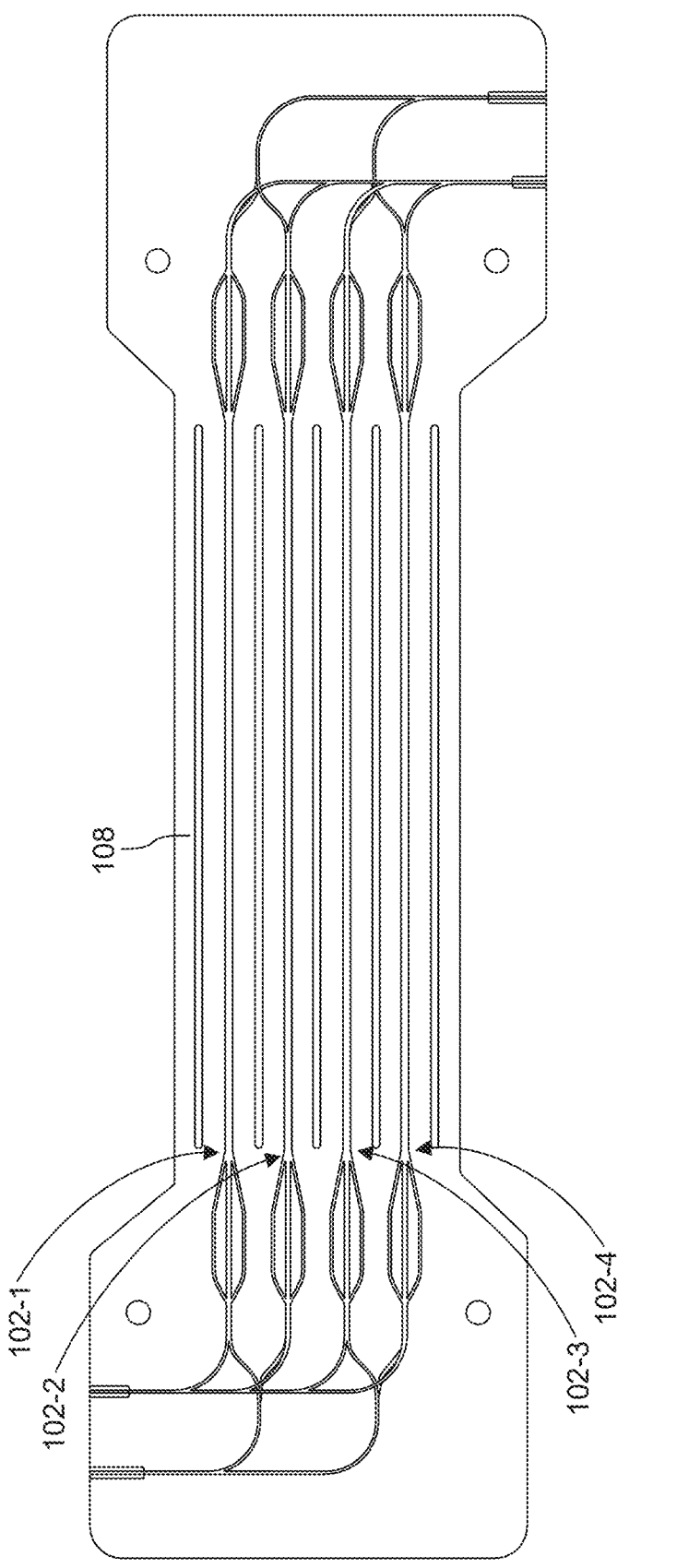
FIG. 8 is a scale plan view of a four parallel channel microchannel system.

FIG. 8 is a scale plan view of a four parallel channel microchannel system comprising four microchannels 102-1 to 102-4 fabricated in a common substrate. Such parallelization could be employed to increase throughput.

Figure 9:
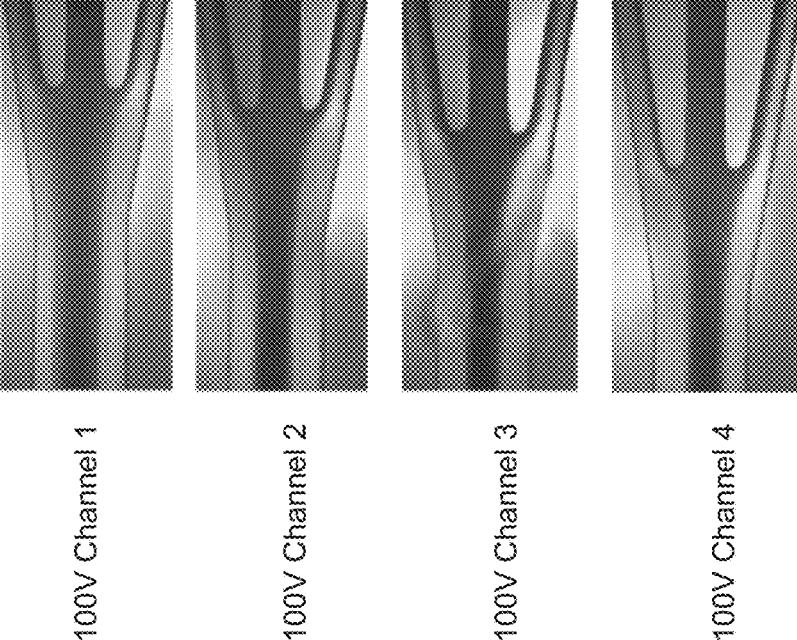
FIG. 9 shows an example of a four parallel channel device showing that another option of scaling up and increasing throughput is by parallel channels (instead of long channel); the images show each channel of a single 4-channel device with 100V applied to transducer.

FIG. 9 shows an example of the four parallel channel device of FIG. 8 to illustrate that another option of scaling up and increasing throughput is by parallel channels (instead of long channel). The images show each channel of a single 4-channel device with 100V applied to transducer. Packed red blood cells in buffer are the sample, which shows up as the dark fluid in the channel. The red blood cells are acoustically focused from the sides of the channel, where they are introduced, to the center at the outlet, as shown.

Figure 10:
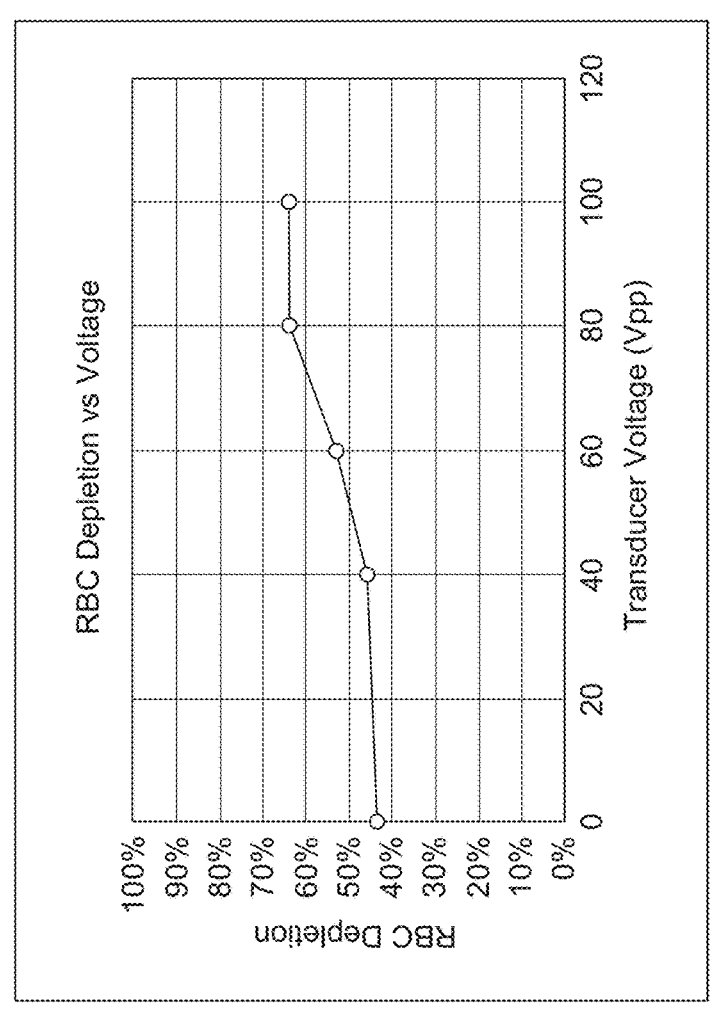
FIG. 10 is a plot of red blood cell depletion as a function of voltage.

FIG. 10 is a plot of red blood cell depletion as a function of voltage corresponding to the images shown in FIG. 9.

A number of experiments were performed.

Electroporation of T cells with mRNA was performed in the microfluidic channel to demonstrate precise control over what buffer the T cells are exposed to by using acoustics to move them into different channel locations. For successful electroporation to occur, T cells needed to be in the BTX electroporation buffer containing mRNA when exposed to an electric field between the electrodes. It is recommended by the manufacturer to limit time of exposure to the BTX electroporation buffer to no more than 15 minutes or else it may be harmful to the cells. Based on the input flow rate of the T cells and the geometry of the channel, we estimate that the T cells completely pass through the channel after approximately 2 seconds. When acoustics are turned on, the T cells cross over into the center stream before the midpoint of the channel. As a result, T cells are only exposed to the BTX buffer for approximately less than 1 second before exposure to an electric field for electroporation. Then the output is plated into growth media within minutes of collection, which dilutes out the BTX electroporation buffer and minimizes the time exposed to the electroporation buffer.

The T cells were introduced into the sheath, and BTX containing 50 μg/ml mCherry mRNA into the center. Then different electrical pulses were tested to obtain a range of electroporation efficiencies. Electrical biphasic pulses with voltages of V=20, 25, 30, and 35 V, pulse duration of τ=250 μs, and pulse frequency of f=150 Hz were applied to the system. At this frequency cells are exposed to approximately 4 pulses at the flow rate they travel through the channel. Each condition was repeated with the acoustic force turned off to keep the T cells in PBS, and with the acoustic force turned on to move the T cells into the BTX and mRNA. The collected output samples were plated into media and analyzed by flow cytometry 24 hours after electroporation. Representative flow cytometry plots show the gating strategy used to obtain viability and electroporation efficiency measurements in FIG. 11. Relative viability (viability ratio) and electroporation efficiency was plotted against the optimal electric field (FIGS. 12A and 12B). The ideal electric field values were calculated by E=V/w, where w here is the width of the center stream. The ideal field was expected if there was no mixing between the high conductivity PBS sheath, and low conductivity BTX center stream. However, due to diffusion, the average electric field is lower. The plotted data is an average of three separate electroporation experiments performed on separate days, using three independent and healthy T cell donors. With the acoustic excitation turned off, T cells remained in the PBS sheath, and there was consistently no electroporation even at the highest applied electric fields. With the acoustic excitation on, T cells were moved into the BTX with mRNA, and electroporation efficiency increased monotonically from 20% to 60% as the electric field increased. The viability ratio was main tained to be consistently high between 0.85 to 0.95. The presence of acoustic excitation had no obvious adverse impact on the viability of the T cells.

Figure 11:
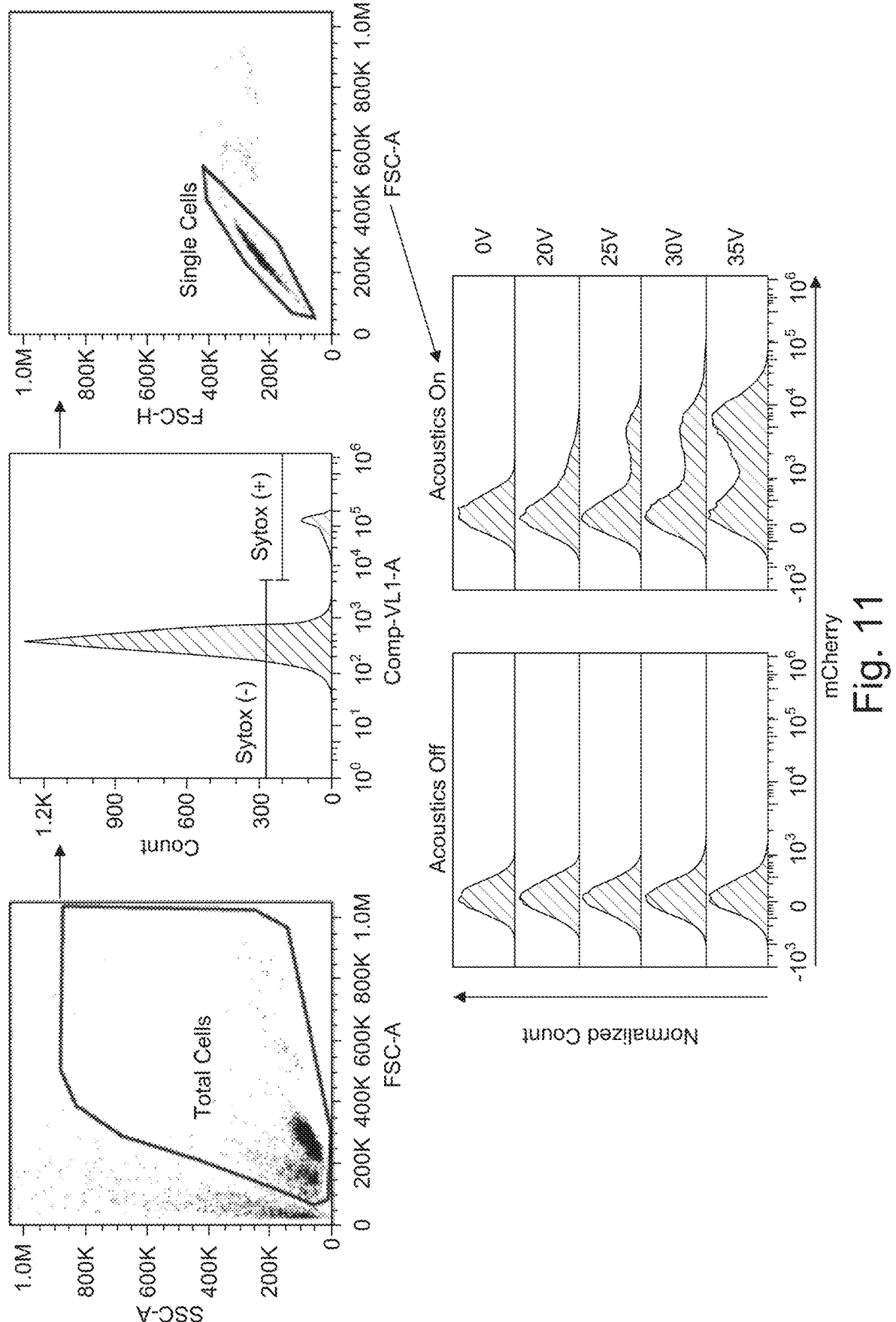
FIG. 11 shows representative flow cytometry plots for experiments.
Figure 12A:
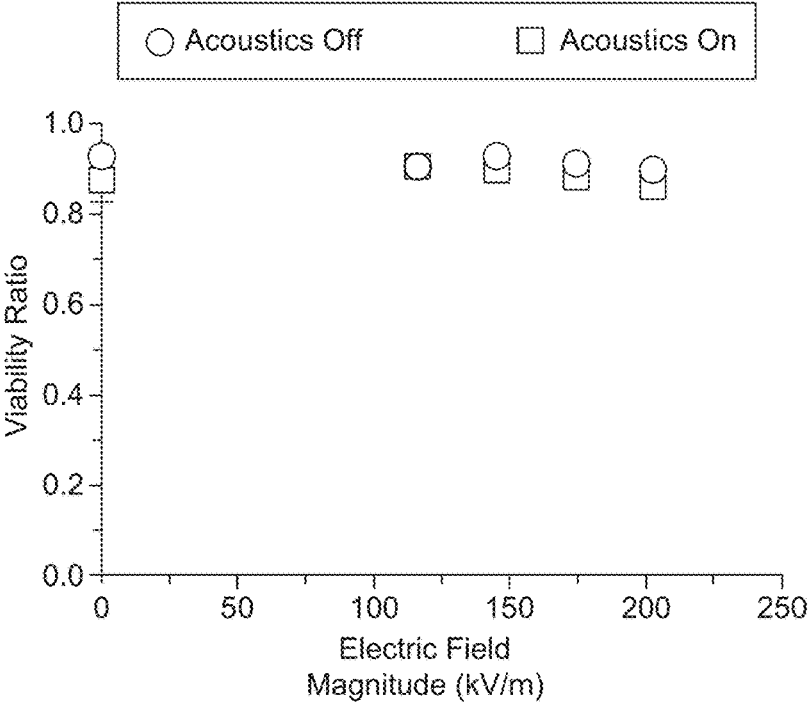
FIG. 12A shows the Viability Ratio defined as the viability at 24 hours divided by initial pre-electroporation viability plotted against the optimal electric field magnitude.
Figure 12B:
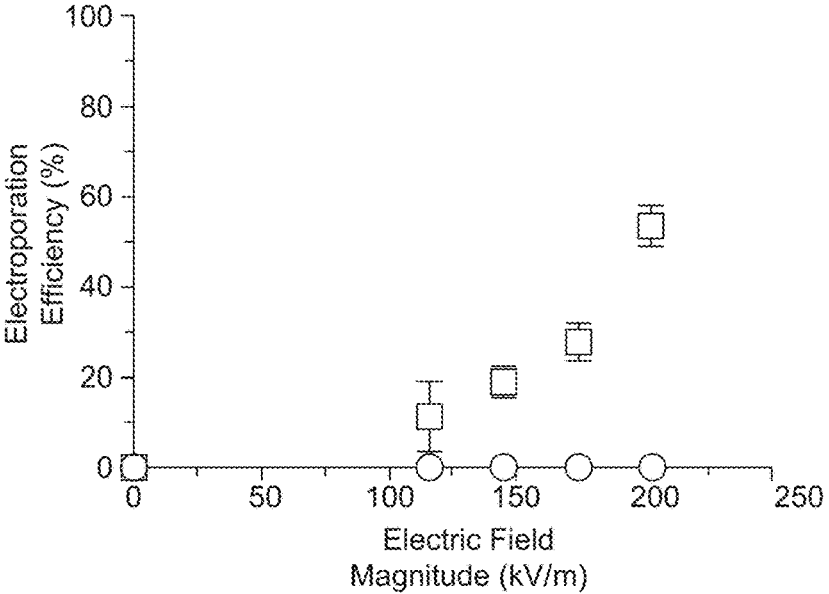
FIG. 12B shows the Electroporation efficiency, the percentage of mCherry positive cells, plotted against the optimal electric field magnitude. The error bars represent the standard error mean.

FIG. 11 shows representative flow cytometry plots to show the gating strategy used for analysis. The viability was calculated as the percentage of Sytox negative cells within the total cell population. The mCherry positive and negative populations were calculated from the single, live cell population. The mCherry flow histograms of acoustics off and on samples show a larger positive peak as voltage is increased.

FIG. 12A shows the Viability Ratio defined as the viability at 24 hours divided by initial pre-electroporation viability plotted against the optimal electric field magnitude.

FIG. 12B shows the Electroporation efficiency, the percentage of mCherry positive cells, plotted against the optimal electric field magnitude. The errors bars represent the standard error mean.

While this invention has been particularly shown and described with references to preferred embodiments thereof, it will be understood by those skilled in the art that various changes in form and details may be made therein without departing from the scope of the invention encompassed by the appended claims. For example, an application for this invention in electrotransfection was described in detail, but other uses of this invention are possible. For example, polymer microparticles can be functionalized by sequential exposure to different reagents, such as silane, followed by GMBS, followed by a biologically active protein.

What is claimed is:

1. A method for sequential exposure of particles to different fluid streams, comprising:
   flowing a first fluid and a second fluid through a microchannel device of one or more substrates;
   acoustically moving particles in the first fluid to the second fluid, while the first and second fluids flow parallel to one another with an acoustic transducer of the microchannel device;
   electroporating the particles in the microchannel device after the particles have been moved into the second fluid with electroporation electrodes downstream of the acoustic transducer; and thereafter
   moving the particles out of the second fluid.

2. The method of claim 1, further comprising controlling residence times of the particles in the second fluid.

3. The method of claim 1, wherein the first fluid and the second fluid are merged in a laminar flow regime.

4. The method of claim 1, wherein the first fluid is a cell buffer and the second fluid is an electroporation buffer.

5. The method of claim 1, wherein the particles are moved out of the second fluid back into the first fluid.

6. The method of claim 1, wherein the particles are moved out of the second fluid and into a third fluid.

7. The method of claim 1, wherein the particles are acoustically moved out of the second fluid by a second acoustic transducer downstream of the electroporation electrodes.

8. A method for sequential exposure of particles to different fluid streams, comprising:
   directing a first flowing fluid containing particles and a second flowing fluid through a microchannel device of one or more substrates;
   supplying acoustic radiation to acoustically move particles from the first flowing fluid to the second flowing fluid with an acoustic transducer of the microchannel device;
   electroporating the particles in the microchannel device after the particles have been moved into the second flowing fluid with electroporation electrodes down-stream of the acoustic transducer; and thereafter moving the particles out of the second flowing fluid, wherein, the second flowing fluid forms a central stream and the first flowing fluid forms a side stream of a sheath flow configuration.

9. The method of claim 8, wherein the particles are acoustically moved out of the second flowing fluid by a second acoustic transducer downstream of the electropora-tion electrodes.

10. The method of claim 8, wherein:

directing the first flowing fluid and the second flowing fluid comprises flowing the first flowing fluid and the second flowing fluid through the microchannel device;

supplying the acoustic radiation comprises acoustically moving the particles in the first flowing fluid to the second flowing fluid with the acoustic transducer of the microchannel device;

and the microchannel device establishes, in the sheath flow configuration, a sheath flow of the first flowing fluid on either side of the second flowing fluid.

11. The method of claim 10, wherein the particles are acoustically moved out of the second flowing fluid by a second acoustic transducer downstream of the electropora-tion electrodes.

* * * * *